(12) United States Patent
Thomas

(10) Patent No.: US 9,007,053 B2
(45) Date of Patent: Apr. 14, 2015

(54) CIRCUITRY FOR AND A METHOD OF COMPENSATING DRIFT IN RESISTANCE IN EDDY CURRENT PROBES

(75) Inventor: Andrew Thomas, Westford, MA (US)

(73) Assignee: Olympus Scientific Solutions Americas Inc.

( * ) Notice: Subject to any disclaimer, the term of this patent is extended or adjusted under 35 U.S.C. 154(b) by 349 days.

(21) Appl. No.: 13/435,706

(22) Filed: Mar. 30, 2012

(65) Prior Publication Data

US 2013/0257415 A1    Oct. 3, 2013

(51) Int. Cl.
*G01R 35/00* (2006.01)
*G01N 27/90* (2006.01)

(52) U.S. Cl.
CPC .................................. *G01N 27/9046* (2013.01)

(58) Field of Classification Search
USPC .......................................................... 324/202
See application file for complete search history.

(56) References Cited

U.S. PATENT DOCUMENTS

| 4,893,079 | A  | * | 1/1990  | Kustra et al.     | 324/225 |
| 5,055,784 | A  | * | 10/1991 | Jaeger et al.     | 324/233 |
| 5,144,231 | A  | * | 9/1992  | Tenenbaum et al.  | 324/164 |
| 5,250,776 | A  | * | 10/1993 | Pfaffmann         | 148/509 |
| 6,288,536 | B1 | * | 9/2001  | Mandl et al.      | 324/225 |
| 6,479,990 | B2 | * | 11/2002 | Mednikov et al.   | 324/225 |
| 7,317,607 | B2 | * | 1/2008  | Omura et al.      | 361/502 |
| 2004/0075452 | A1 | * | 4/2004  | Hrubes          | 324/721 |
| 2004/0176918 | A1 | * | 9/2004  | Slates           | 702/65  |
| 2008/0246468 | A1 | * | 10/2008 | Lepage et al.   | 324/225 |

* cited by examiner

*Primary Examiner* — Patrick Assouad
*Assistant Examiner* — Demetrius Pretlow
(74) *Attorney, Agent, or Firm* — C. Tricia Liu

(57) ABSTRACT

Disclosed is an eddy current non-destructive inspection device which includes an eddy current probe with a probe conductor resistance dynamically changing due to operation conditions, such as temperature. The device further includes a signal generating circuit generating an inspection frequency signal and a low frequency signal. Sensed inspection frequency signals are processed to produce resulting signals with possible drift. A low frequency processing circuit includes a resistance calculator producing a substantially true value of the dynamic probe resistance, based on which compensation operations are configured to correct the drifted resulting signals and produce corrected resulting signals.

20 Claims, 4 Drawing Sheets

CIRCUITRY FOR AND A METHOD OF COMPENSATING DRIFT IN RESISTANCE IN EDDY CURRENT PROBES

FIELD OF THE INVENTION

The present invention relates to non-destructive testing (NDT) and more particularly to an eddy current array (ECA) probe or an eddy current (EC) probe.

BACKGROUND OF THE INVENTION

An EC probe is normally manufactured using an electric conductor and winding it into a coil. The conductor has electric resistance, and this conductor resistance becomes an unwanted part of the measurement. This is because part of the conductor resistance can be often confused with the EC measurements being made. A typical instrument needs to be calibrated by the user at the start of operation to remove as much as possible the effects of the probe conductor resistance. However, the task of eliminating the effect of EC probe conductor resistance becomes challenging because the resistance is a function of temperature. As the operational temperature changes, the probe conductor resistance changes, introducing changes in measurement results unknown to operator and therefore un-accounted for during the calibration procedures. As a result, the EC measurement that the instrument performs becomes less accurate.

A typical EC instrument applies an alternating current in the range of 1 KHz to 12 MHz to the probe coil. By measuring the probe voltage and current components in phase and 90 deg to the voltage phase, the resistance and the inductance of the probe can be calculated, if there are no errors caused by factors such as temperature change.

In an existing practice, to make a typical measurement or inspection of a test sample, for example, an aluminum plate, the operator would place the probe against the plate. The EC instrument will generate an alternating current and then measure the inductance and the resistance in the EC probe (hereinafter as the measured inductance and the measured resistance). The eddy current induced into the test piece, bucks the field of the probe, and thus the field is squeezed into a smaller space. A smaller magnetic field requires less energy to generate. Less energy being used implies that the instrument will measure less inductance in the EC probe.

The EC instrument measures the energy lost during the measurement. The test sample in which the eddy current flows is not a perfect electrical conductor and therefore responsible for a portion of the energy loss in this process. The EC instrument's measured resistance actually represents the probe conductor resistance, plus the resistance to the eddy current in the test sample. The EC instrument measurement of resistance can not distinguish between the energy lost by the test sample resistance, and the energy lost by the probe conductor resistance. In existing practice, the change in the probe conductor resistance is not accounted for, and therefore the change in energy lost in the probe conductor resistance is also not accounted for.

In order to overcome the inaccuracy caused by the above described factors, and to measure the eddy current energy loss accurately, the instantaneous probe conductor resistance must be known. It would be preferable if the instantaneous probe conductor resistance or the amount of change from a baseline can be presented to the instrument display and/or accounted for in an algorithm to calculate the energy lost by the eddy current in the test sample.

Existing practice has been seen in U.S. Pat. Nos. 4,893,079 and 6,541,963 in efforts trying to compensate EC inspection drifts caused by temperature change.

U.S. Pat. No. 4,893,079 describes a method for measuring physical characteristics of an electrically conductive material by the use of eddy current techniques and compensating measurement errors caused by changes in temperature. It includes a switching arrangement connected between primary and reference coils of an eddy current probe which allows the probe to be selectively connected between an eddy current output oscilloscope and a digital ohm-meter for measuring the resistances of the primary and reference coils. The changes in resistance due to temperature effects are taken into account while determining the eddy current measurement. However, the need for the extra reference coil in this patent increases the size and the cost of the probe and limits the range of the inspection that the probe can access to.

U.S. Pat. No. 6,541,963 describes an EC transducer capable of enhancing the measurement accuracy by compensating for temperature errors, increasing the resolution and noise immunity. The primary detector in this differential EC transducer incorporates two similar search coils and an additional coil, which presents a similar drawback as seen in U.S. Pat. No. 4,893,079.

The invention described here employs neither the additional coils nor the modifications made to the EC transducer per U.S. Pat. No. 6,541,963. It instead employs a single coil probe and addresses the problem on the EC instrument side by using a low frequency signal generator.

Thus it would be advantageous to provide an EC system with a probe that can compensate the affect of temperature change without the need for an additional coil or an extra bridge circuit as seen in existing efforts.

SUMMARY OF INVENTION

The invention disclosed herein enables the accurate and dynamic measurement of EC probe circuit resistance and the amount of energy lost in the EC coils, and therefore allows the improved accuracy in eddy current measurement whereas existing practice lacks an efficient approach to measure the dynamically changing EC probe circuit resistance.

It should be noted that the terms "probe", "transducer", and "sensor" used herein may be used interchangeably. The terms "device", "instrument", and "system" all denote to the EC non-destructive inspection assembly related to the present disclosure, and may be used interchangeably.

It should also be noted that, "adaptive coil resistance", "dynamic coil resistance", "conductor resistance", or "wire resistance" disclosed and used in the present disclosure denotes to the instantaneous electrical conductor resistance of a specific EC probe under a specific operational condition.

Accordingly, it is a general objective of the present disclosure to enable the EC instrument to produce more accurate measurement results based on dynamic coil resistance in accordance with the specific operational conditions.

The present disclosure includes a method that achieves the above objective by passing a low frequency or a direct current through the EC probe coil and measuring the voltage at the same time the probe is being used to do the inspection. The circuitry applied with low frequencies is not affected to a significant degree by the inductance of the circuitry or the properties of the test object. Therefore the circuitry applied with low frequencies only exhibits the probe conductor resistance, which is subject to changes in operational conditions, such as temperature.

The present disclosure also includes a circuitry that achieves the above objective by applying two different frequencies simultaneously to the instrument which can measure two resistance values at the same time in the same probe. With the conductor resistance measured using the low frequency known; its effect can be subtracted out of the measurement concurrently being made at the higher frequency. The result is a measurement that is corrected for temperature changes or other causes at the time the measurement is being made.

The probe conductor resistance is a good indicator of the temperature of the wire and therefore the temperature of the most of the other parts of the probe. Ferrite for example has a very significant temperature coefficient. Ferrite is often used in EC probe designs to increase the inductance and the shape of magnetic field to improve coupling to the test sample. Ferrite properties experience pronounceable changes as the temperature changes. If the EC probe containing ferrite has been characterized over the operating range of temperature, then the instrument can compensate for most of the change by taking into account the ferrite temperature inferred from the known probe conductor resistance.

BRIEF DESCRIPTION OF THE DRAWING(S)

DETAIL DESCRIPTION OF THE PREFERRED EMBODIMENT

The table below provides reference to the symbols used in the present disclosure.

| Variable | Definition |
|---|---|
| $R_p$ | Probe Conductor Resistance |
| $L_p$ | Probe Inductance |
| $R_x$ | Test Sample Resistance |
| $L_x$ | Test Sample Inductance |
| $R_s$ | resistance of Resistor 103 |
| R | total resistance of the probe circuit |
| L | total inductance of the probe circuit |
| $f_H$ | inspection frequency (frequency of the signals generated by the Inspection Signal Generator 101) |
| $f_L$ | low frequency (frequency of the signals generated by the Low Frequency Signal Generator 201) |

Figure 1:
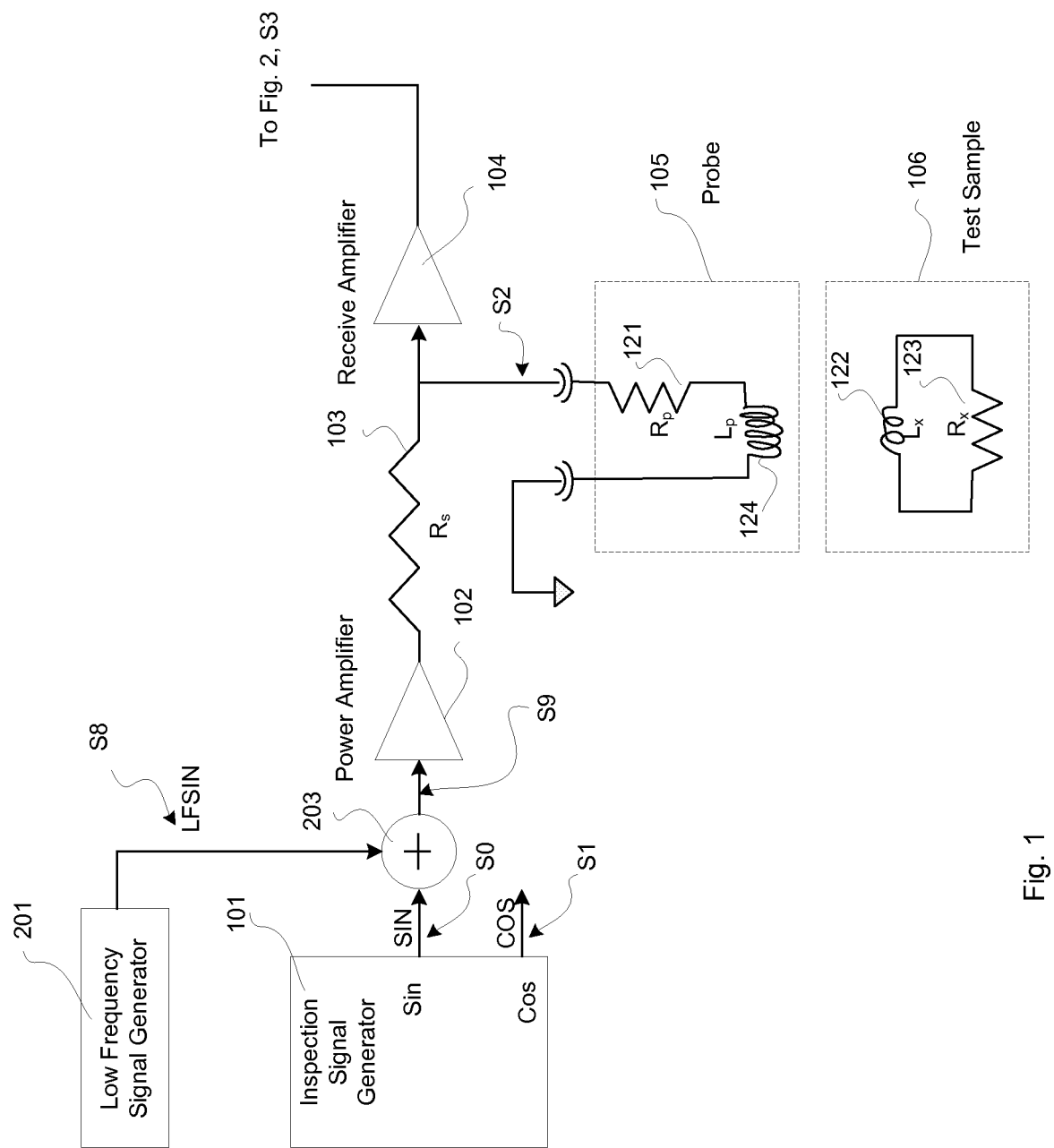
FIG. 1 is a schematic diagram of the signal generating part of the circuitry of an EC instrument according to the preferred embodiment of the present disclosure.

Referring to FIG. 1, the "acquisition" or "receiving" part of the circuitry of an EC instrument according to the preferred embodiment comprises a Low Frequency Signal Generator 201, an Inspection Signal Generator 101, an Adder 203, a Power Amplifier 102, a Resistor 103 ($R_s$), a Receiver Amplifier 104, a Probe 105, and a Test Sample 106.

Test Sample 106 is placed under Probe 105 for eddy current inspection or testing. Inside Probe 105, 121 represents Probe Conductor Resistance ($R_p$) and 124 represents Probe Inductance ($L_p$). Inside Test Sample 106, 123 represents Test Sample Resistance ($R_x$) and 122 represents Test Sample Inductance ($L_x$).

It should be noted that Low Frequency Signal Generator 201 and Adder 203 are the added components in comparison to a prior art design of the receiving part of an EC probe used in existing practice, representing part of the novel aspect of present disclosure.

Figure 2:
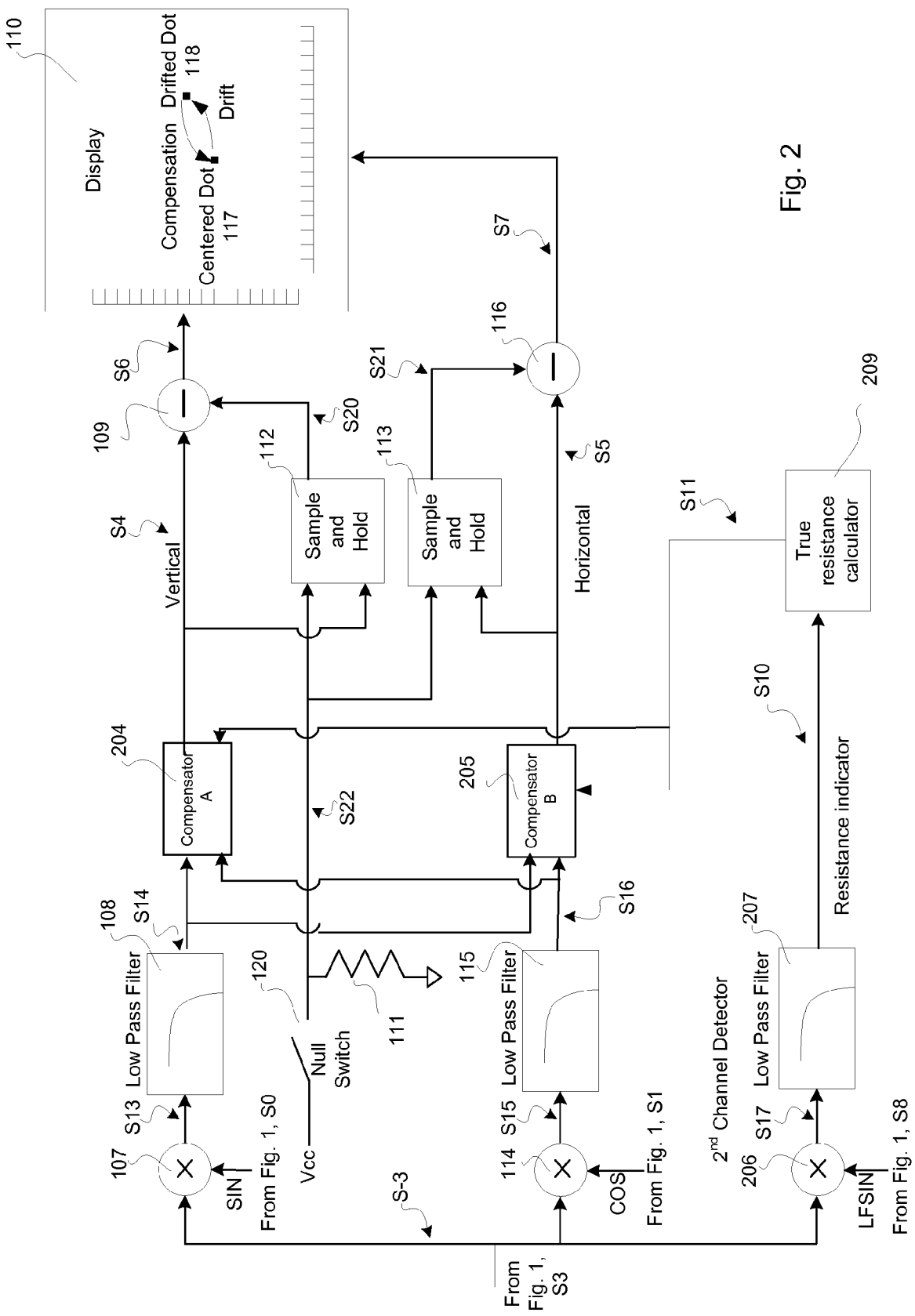
FIG. 2 is a schematic diagram of the "signal processing" part of the circuitry of an EC instrument according to the preferred embodiment of the present disclosure.

Reference is now made to FIG. 2. The signal processing part of the circuitry, dedicated to measuring the REAL part of the complex impedance of the probe circuit, of an EC instrument according to the preferred embodiment comprises a Multiplier 107, Low Pass Filter 108, compensator 204, Subtractor 109, Sample and Hold Unit 112. The signal processing part of the circuitry, dedicated to measuring the REAL or horizontal part of the complex impedance of the probe circuit, includes Multiplier 114, Low Pass Filter 115, compensator 205, Subtractor 116, and Sample and Hold Unit 113. The signal processing part of the circuitry, dedicated to isolating the Probe Conductor Resistance, includes Multiplier 206, Low Pass Filter 207, and resistance calculator 209. The Null Switch 120 and Resistor 111 are common components used to activate Sample and Hold Units 112 and 113. The Display 110 presents the compensated complex impedance (Real and Imaginary) in an X-Y plane to the user of the instrument.

Located on the Display 110, Centered Dot 117 represents the initial position established as part of the EC instrument application calibration process. Drifted Dot 118 represents the drifted position due to the change in operational conditions such as temperature. The present disclosure provides a compensation method to bring the Drifted Dot 118 to the desired position Centered Dot 117.

It should be noted that compensators 204 and 205, Multiplier 206 with its downstream Low Pass Filter 207, and resistance calculator 209 are components representing part of the novel aspect of the present disclosure in comparison to a prior art design of the signal processing part of an EC instrument used in existing practice.

The signals of this circuitry and the related signal processing are described as follows.

Referring back to FIG. 1, the signal path starts at the Inspection Signal Generator 101, which produces two signals, Sine Signal S0 (SIN) and Cosine Signal S1 (COS) of the same frequency, namely $f_H$. $f_H$ is a typical inspection frequency and is adjustable over the range of 1 KHz to 12 MHz. SIN Signal S0 is fed thru Adder 203 into Power Amplifier 102, which subsequently boosts the signal power and feeds to the next stage thru Resistor 103.

Input to the Receive Amplifier 104 is the Combined Probe Signal S2 received from Probe 105. Combined Probe Signal S2 is complex, in that it contains some voltage in phase with SIN Signal S0 representing the resistive component of the probe impedance, and a portion in phase with COS Signal S1 representing the inductive component of the probe impedance. As Probe 105 is moved closer to Test Sample 106, the measured inductance is reduced and the measured resistance is increased due to: 1) the properties of Test Sample 106, and 2) changes in Probe Conductor Resistance $R_p$ 121. It should be noted that $R_p$ 121 is the probe conductor resistance that varies with the temperature.

Subsequently, Combined Probe Signal S2 is amplified by Receive Amplifier 104 to produce an amplitude adjusted Combined Receive Signal S3.

Reference is now made to FIG. 2. Combined Receive Signal S3 is the input of the first Multiplier 107 which functions as the IMAGINARY component detector. Multiplier 107 multiplies the Combined Receive Signal S3 with Sine Signal S0 (shown in FIG. 1), to produce the Detected IMAGINARY Signal S13. Detected IMAGINARY Signal S13 is filtered by Low Pass Filter 108 to produce the Filtered IMAGINARY Signal S14. Compensation operation A is then provided by compensator 204 and applied to the Filtered IMAGINARY Signal S14, to produce the Compensated IMAGINARY or vertical Signal S4.

Combined Receive Signal S3 is the input of the second Multiplier 114 which functions as the real component detector. Multiplier 114 multiplies the Combined Receive Signal S3 with Cosine Signal S1 (shown in FIG. 1), to produce the Detected REAL Signal S15. Detected REAL Signal S15 is filtered by Low Pass Filter 115 to produce the Filtered REAL Signal S16. Compensation operation B is given by compensator 205 is then applied to the Filtered Real Signal S16, to produce the Compensated Real or horizontal signal S5.

Since an EC instrument operator is usually interested in the changes to the Compensated Real and Compensated Imaginary signals, S5 and S4 respectively, a means is provided to subtract their sampled values from these signals so that the Centered Dot 117 is moved to the center of the Display 110. Centering the dot on the display (also referred as the nulling process) is usually done as part of the EC instrument application calibration process. The subsequent movement of the Centered Dot 117 on the Display 110 will be monitored as part of the EC inspection process and interpreted as the measurement results. Therefore, it is critical that any movement of the Centered Dot 117 is due to the properties of Test Sample 106, and not due to the other factors such as temperature changes.

Similar to existing practice, the preferred embodiment also includes a mechanism for the nulling process described as follows. When Null Switch 120 is open, the Latching Signal S22 would be at logic low due to the Resistor 111 connected to ground. When Null Switch 120 is closed, by the operator initiating the nulling process, the Latching Signal S22 would go to logic high due to the side connected to power $V_{cc}$. This transition of Latching Signal S22 (logic low to logic high) causes the current values of the Compensated IMAGINARY S4 and Compensated REAL S5 signals to get captured and stored inside the Sample and Hold Units 112 and 113 respectively. The stored value, Sample and Hold IMAGINARY Signal S20 is then subtracted from the Compensated IMAGINARY Signal S4, through Subtractor 109 to produce the Vertical Control Signal S6. The Vertical Control Signal S6 is used to control the vertical position of the signal (the Centered Dot 117) on the Display 110. Similarly the other stored value, Sample and Hold REAL Signal S21 is then subtracted from the Compensated REAL Signal S5, thru Subtractor 116 to produce the Horizontal Control Signal S7. The Horizontal Control Signal S7 is used to control the horizontal position of the signal (the Centered Dot 117) on the Display 110. The new position of the Centered Dot 117 will be in the center of the Display 110, thereby completing the nulling process. Now the dot movements on the display would ideally correspond to the changes in the measured resistance and the measured inductance.

Reference is now made to FIG. 1. One of the novel aspects of the preferred embodiment includes a second signal channel added to provide a low frequency signal into the system. A Low Frequency Signal Generator 201 produces the Low Frequency Signal S8 (LFSIN) with a frequency, namely $f_L$, much lower than the inspection frequency $f_H$. If the frequency $f_L$ is too low, it could cause the Centered Dot 117 to jitter. If the frequency $f_L$ is too high, the measured resistance may not provide the desired independence from the Test Sample 106. A frequency of 100 Hz is expected to work well for most probes.

Preferably, an Adder 203 is used to add the Sine Signal S0 (with frequency $f_H$) to the Low Frequency Signal S8 (with frequency $f_L$), to produce the Combined Generated Signal S9. From this point on, in the subsequent parts of the circuitry of the preferred embodiment, both signals reside in the combined signal that propagates thru the system. Both of these signals function in the same parts of the circuitry at the same time, separated only by their frequencies. The Combined Generated Signal S9 is subsequently provided as the input to the Power Amplifier 102.

It should be noted that when compared with the existing practice, the Combined Generated Signal S9 in this preferred embodiment is processed and passed through the main channel of the circuitry, from the Inspection Signal Generator 101 in FIG. 1 up to the compensators 204 and 205 in FIG. 2, in the same way as if the Low Frequency Signal S8 had not been added, which would be the case in the existing practice.

Therefore the low frequency component (signal S8) of the Combined Generated Signal S9 passes through the Power Amplifier 102 and Resistor 103 to Probe 105. The low frequency component (signal S8) of the Combined Probe Signal S2, received at the Receive Amplifier 104 corresponds to the Probe Conductor Resistance $R_p$ 121 of Probe 105. Because the frequency of signal S8, $f_L$ is low, the low frequency component in signal S2 contains largely the real component, with no significant imaginary component. The Combined Probe Signal S2 becomes the Combined Received Signal S3 after processed by the Receive Amplifier 104.

Total resistance R and total inductance L of the probe circuit can be represented as:

$$R = R_p + R_x \qquad \text{Eq. 1}$$

$$L = L_p + L_x \qquad \text{Eq. 2}$$

The signal output at S3 contains two portions which can be presented as follows:

$$\text{High frequency portion of } S3 = f_1(R_x, R_p, L, R_s) \qquad \text{Eq. 3}$$

$$\text{Low frequency portion of } S3 = f_2(R_p, R_s) \qquad \text{Eq. 4}$$

That is to say, high frequency portion of signal the sensed signal S3 responding to inspection frequency $f_H$ is a function of ($R_x$, $R_p$, L, $R_s$). In another word, high frequency portion of signal S3 is related to, among others, test sample resistance, total probe inductance and resistance of resistor $R_s$. Low frequency portion of the sensed signal S3 responding to low frequency signal S8 is a function of probe conductor resistance $R_p$ and is not a function of test sample resistance $R_x$ since the coupling of Probe 105 to Test Sample 106 at such low frequencies is negligible.

Therefore S3, contain a low frequency component that corresponds to true value of probe conductor resistance $R_p$.

Referring now to FIG. 2, the Combined Receive Signal S3 is the input of the third Multiplier 206 which functions as the low frequency component detector. Multiplier 206 multiplies the Combined Receive Signal S3 with the Low Frequency Signal S8 (shown in FIG. 1), to produce the Detected Low Frequency Signal S17. The Detected Low Frequency Signal S17 is filtered by the Low Pass Filter 207 to produce a signal S10 which is directly related to the probe conductor resistance $R_p$ 121.

Signals S16 and S14 are real and imaginary signal components respectively, and also the functions test sample resistance $R_x$, total probe inductance L and resistance of probe conductor resistance R. However signal S10 contains only a low frequency component and is also a function of the Probe Conductor Resistance $R_p$ 121 that varies with the temperature. Therefore, by feeding S10 value into the resistance calculator 209, we can produce base compensation values corresponding to the temperature changes and correct both S14 and S16.

Continuing to refer to FIG. 2, the resistance base signal S10 then passes into the resistance calculator 209 which provides a signal S11 which closely approximates the true value of the probe conductor resistance. Inside resistance calculator 209, a base compensation factor is calculated based on the value of S10 to produce signal S11 representing the approximated true value of the probe conductor resistance $R_p$. An exemplary method of calculating S11 is given by, $$S10*Rs/(1-S10) \qquad \text{Eq. 5}$$

where $R_s$ is the resistance of resistor 103 in shown FIG. 1.

The base compensation value S11, which is effectively the approximated value of true probe resistance $R_p$, is then preferably fed to two compensators 204 and 205 to compensate and correct vertical value S14 and horizontal value S16, respectively.

Referring to FIG. 2, in one example, as shown on the Display 110, without compensation, the position of the Centered Dot 117 will drift to the Drifted Dot 118 due to the temperature changes. When applying the compensation method disclosed herein, the Centered Dot 117 will remain still during the temperature changes and therefore the measurement results will be more accurate.

Figure 3:
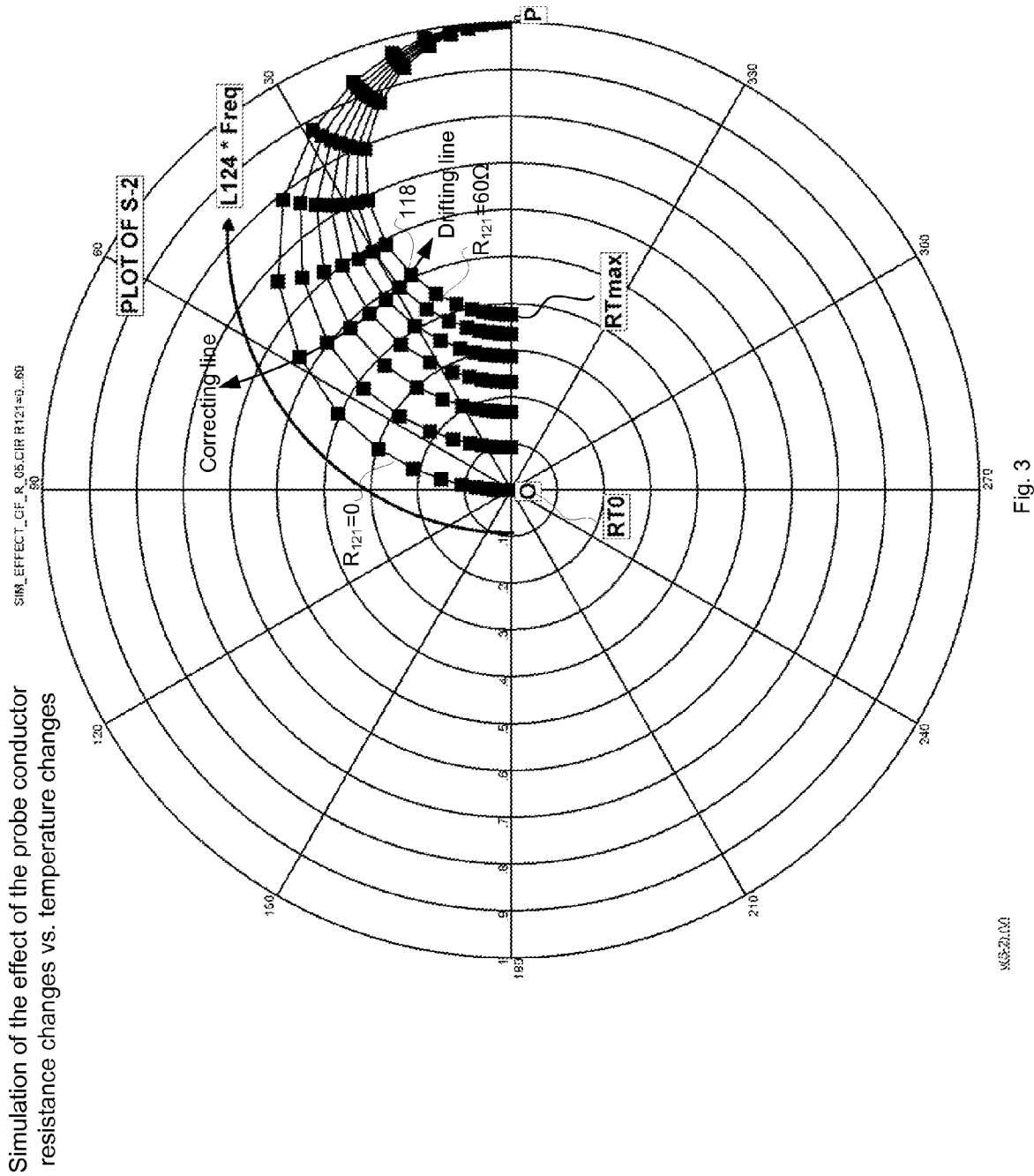
FIG. 3 is an exhibition of signal S2 in a polar coordinate, delineating how the signal drifts with temperature, and how the drift is corrected according to the preferred embodiment of the present disclosure.

The above drifted dot 118 and the corrected centered dot 117 and the method of how the 'drifting' is corrected are elaborated in diagram shown in FIG. 3.

Reference is primarily now made to FIG. 3, with occasional reference back to FIGS. 1 and 2. Signal S2 representing the response of probe circuit 105 is simulated by using an electronics simulation tool SPICE (MICROCAP), which is widely known to those skilled in the art. The resultive S2 data (small black filled squares) is shown in a polar coordinate system. The trajectory and patterns exhibited by the simulated data plotted for signal S2 represent the intrinsic property (resistance Rp 121 and inductance Lp 124) of the commonly used probe circuit 105 under changing operation temperature and inspection frequency, which are all known to those skilled in the art. However, one of the novel aspects of the present disclosure is to correct the temperature drift by using the intrinsic property of signal S2 and with the understanding of how probe circuit 105 behaves as temperature changes.

Therefore before going into any details with regard to the diagram shown FIG. 3, it should be noted that the "temperature drift" as the primary problem aimed to be solved in the present disclosure is represented by the line "correction—drifting". The direction pointing to "drifting" denotes how the probe impedance tends to drift as temperature increases. The direction pointing to "correction" denotes how the corrections are made using the preferred embodiment in the present disclosure. Realizing and finding how the probe impedance drifts and how to correct such drift or how to derive compensation operation for compensator A 204 and compensator B 205 represent some of the novel aspects of the present disclosure.

Signal points similar to dots 117 and 118 represent an example of inspection results, which are functions of, among others, probe inductance Lp 124 and probe resistance Rp 121.

Some brief explanation of the diagram in FIG. 3 is as follows. Again, the simulation result itself is not the scope of the present disclosure and one can refer to SPICE-MICROCAP for a basic simulation of a typical single coil EC probe circuit, such as 105, with resistor 103. Signal S2 shown as small black filled squares represent the response of probe circuit 105 simulated by using MICROCAP when the probe is subject to temperature change from $RT_0$ to $RT_{max}$. Therefore referring to the direction of 'drifting' line, the higher the temperature, the further the signal S2 drifts towards $RT_{max}$. S2 signals traveling along the semi-circles, from point O to P represent the changes in signals with applied inspection frequency. Further the signal pointing away from point O denotes the higher $L124*f_H$ (result of inductance 124 and inspection frequency).

Inductor $L_P$ 124 acts like an open circuit at infinity frequency (point P) in the polar coordinate regardless of the value of R103 and R121, since there is no current through R103 and R121. When inspection frequency (DC) is 0, signal point for S2 moves along its semicircle circumference back to point O.

At the same frequency, the higher the operational temperature, the larger R121 is, the smaller the diameter of semicircle is. For an instance, correcting—drifting line shows how signal S2 changes as R121 increases from 0 ohm to 60 ohm.

Still referring to FIG. 3 and returning back to the problem at issue, which is how to correct drifted S2 signals with compensation operation so that the display is corrected back along an exemplary line "correction line".

As can be seen in FIG. 3, skilled in the art can employ the simulation result to determine the values associated with $RT_0$ and $RT_{max}$. Since $RT_{max}-RT_0$ is a function of S11, one can define the correction width between maximum temperature and zero temperature. One can also define the pattern and trajectory of each specific S2 signal semi-circle line for each specific operation temperature. Geometric transform and deduction can then be employed to define the correction line to be normal to the specific semi-circle at each specific $Lp*f_H$.

Exemplary compensation method employed by the preferred embodiment is to extract the approximation of the instant probe conductor resistance value S11 and use compensators 204 and 205 to carry out for following two operations, COMPA and COMPB, respectively.

$$COMPA=S16*R_S/((1-S14)^2+S16^2)*2*\pi*f_b \qquad \text{Eq. 6}$$

$$COMPB=[(1-S14)/\sqrt{((1-S14)^2+S16^2)}-S11-\sqrt{((1-S14)^2+S16^2)}]*R_S/\sqrt{((1-S14)^2+S16^2)} \qquad \text{Eq. 7}$$

wherein the symbols in Eqs. 6 and 7 are denoted by Table-1 or FIG. 2.

It should be noted that the signal points for S2 in FIG. 3 can be presented as voltage at S2, or other parameters at S2, which does not affect the scope of the present disclosure. Any simulation or experiment result exhibiting the intrinsic effect of temperature and inspection frequency on the signals of concern can be employed to deduce the method of correcting such effect of temperature on the drifted inspection result. The compensation operations derived above only serves as one of the examples for such temperature correction. It should be appreciated that any other geometric or algorithmic derivations aimed at finding the reversed course of temperature effect on eddy current probe are within the scope of the present disclosure. As such, the diagram in FIG. 3 can be in the form of any descriptor, such as a chart, table or formula which describes the effect of temperature on the EC circuit of concern. They can be provided on board during a design phase, or later provided corresponding to the probe being used by any external source, such as a flash memory or keyboard entry.

It should also be noted that the exemplary diagram shown in FIG. 3 is only one of the options that can be used to derive the compensation operation based on the instant true value given by signal S11.

One should also appreciate that herein disclosed method can be naturally extended to EC probe circuits with multiple EC coils or arrays. One can use similar electronic simulations to establish the effect of temperature and inspection frequency on the resultive inspection signals and further deduce the reversal course to correct the drift caused by operation temperature for probes with other type of coil structures.

It should also be noted that the MICROCAP simulation mentioned above is done without including a cord or cable of the probe. Those skilled in the art should appreciate that the simulation result and geometric presentation of the inspection signal for S2 may have a different form and corresponding correcting line. The definition and deduction of the corresponding correcting line are with within the scope of the present disclosure for situations when a probe cord or cable is included.

Figure 4:
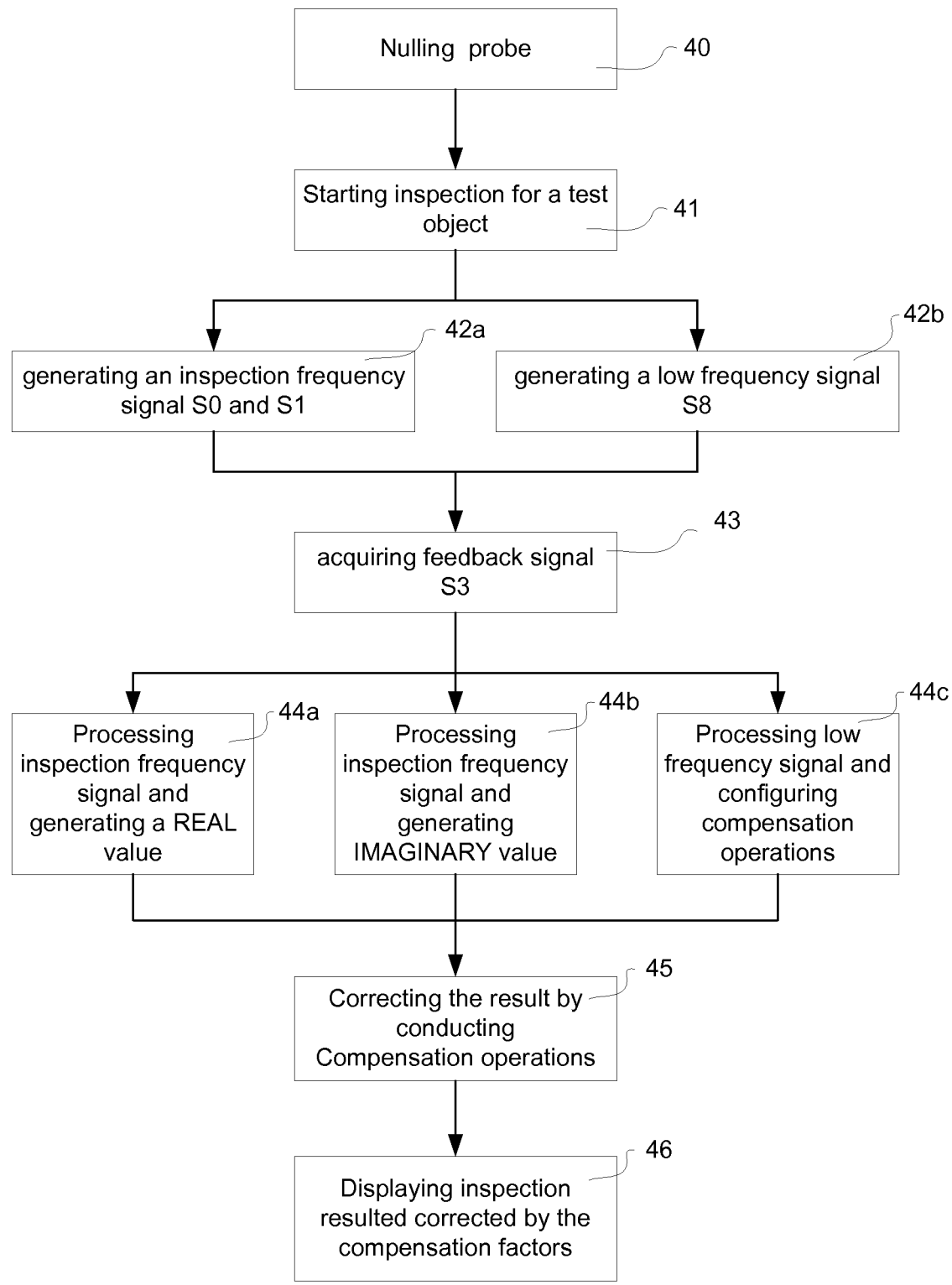
FIG. 4 is a schematic flow chart diagram showing the process of correcting the temperature drift employed by the using the preferred embodiment.

Reference is now made to FIG. 4, which describes a method and the associated process of correcting temperature related resistance drift by the using the preferred embodiment as shown in FIGS. 1, 2 and 3. The process and steps herein described is intended to present the scope of the novel method of the present disclosure. It is not intended to be completely inclusive of all possible steps that could be employed, executed or implemented by the apparatus shown in FIGS. 1~3.

Referring primarily to FIG. 4, assisted by referring back to FIGS. 1~3, in step 40, probe 105 is engaged with test sample 106 and an inspection session is ready to be started. In step 41 the EC instrument is nulled by pressing null switch 120 in FIG. 2. In parallel steps 42a and 42b, the EC instrument generates inspection signals (S0 or S1) and a low frequency signal, respectively. Additionally, in step 43, the response of inspection frequency signal and low frequency signal are processed and acquired as signal S3. In steps 44a and 44b, the acquired feed back signal S3 and inspection frequency signals are processed to produce a REAL and an IMAGINARY resulting signal respectively. In step 44c, the acquired signal S3 and low frequency signal S8 are used and processed to produce a close approximation of the true value of the probe conductor resistance S11. And S-11 is used among other factors to configure at least one compensation operation. In step 45, the compensation operations are used to correct the REAL and IMAGINARY values from steps 44a and 44b. In step 46, the EC instrument displays the inspection results corrected through the compensation operation.

Alternate Embodiments

In an alternative embodiment, the inspection signal generator can be devised so that it normally generates inspection signals at the inspection frequency, and also at certain operational intervals, it generates a low frequency signal for a short moment to enable the measurement of the probe conductor resistance. It may be possible to do this without noticeable interruption of normal operation and therefore the low frequency signal generator can be negated. The alternative embodiment allows modifying the existing system designs to have their software updated without requiring any change to the hardware.

Another alternative embodiment involves adapting the presently disclosure to a multi-frequency EC inspection application. The approximate true value of the probe resistance can be used to compensate more than one inspection frequency processing circuits. It can be appreciated by those skilled in the art that the alternation is within the scope of present disclosure.

Yet another alternative embodiment can be devised so that the low frequency signal is a DC signal for signal S8 in FIG. 1. It can be easily recognized by the skilled in the art that the present disclosure applies to using DC signal to achieve the approximation of true probe resistance and further correct the resistance drift.

In the foregoing embodiments, the EC sensors have been described and depicted as being single coil windings. However, as can be recognized by one of skilled in the art, the present disclosure also applies to other types of EC sensors or EC array sensors with their resistance affected by operation temperature.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An eddy current non-destructive inspection device comprising,
    at least one eddy current probe having a probe circuit including coil components, wherein the passage of a probe current through the probe circuit is effective to induce eddy currents in a test object when the probe and the test object are coupled and the probe is effective to sense the eddy currents, wherein the probe circuit has a dynamically changing probe resistance;
    a signal generating circuit generating at least one inspection frequency signal and a low frequency AC signal and processing the sensed eddy currents to sensed signal, wherein the at least one inspection frequency signal affects the eddy currents and the sensed signal;
    a signal receiving and processing circuit operable for processing the sensed signal and producing resulting signals with a signal drift caused by change in coil conditions including temperature change, wherein the processing circuit further comprising at least one compensator;
    a low frequency coil monitoring circuit including a detector for detecting the low frequency AC signal, a low pass filter and a resistance calculator processing the low frequency signal and producing a compensated value of the dynamic probe resistance with the signal drift annihilated, and,
    wherein the at least one compensator is configured to correct the resulting signals and produce corrected resulting signals based on at least one predetermined compensating operation that includes the compensated value of the dynamic probe resistance.

2. The eddy current non-destructive inspection device in claim 1 wherein the inspection signal and the low frequency signal and their corresponding resulting signals co-exist within at least a part of the signal generating circuit and the processing circuit.

3. The eddy current non-destructive inspection device in claim 1 wherein the probe circuit, when under the affect of the passing current, presents a complex impedance which include the dynamically changing probe resistance and inductance in the probe circuit, wherein the coupling of the probe and the test object is a function of the inductance in the probe circuit.

4. The eddy current non-destructive inspection device in claim 3, wherein the resulting signals including a first and a second resulting signal which are processed by a first inspection frequency processing portion and a second inspection processing portion, respectively.

5. The eddy current non-destructive inspection device in claim 4, wherein the compensation operation is to correct the first resulting signal and the second resulting signal in processing circuit.

6. The eddy current non-destructive inspection device in claim 4, wherein the compensation operation is derived partly from a descriptor exhibiting the effects of temperature changes on the probe circuit.

7. The eddy current non-destructive inspection device in claim 6, wherein the descriptor is a chart, table or formula which is derived from an electronic simulation or experiment on at least part of the signal generating circuit, wherein the descriptor can be stored on the device, or provided from any external source.

8. The eddy current non-destructive inspection device in claim 4, wherein the at least one compensation operation is configured according to the compensated value of the dynamic probe resistance and at least one of the following:
   a) the first resulting signal;
   b) the second resulting signal;
   c) the inspection frequency.

9. The eddy current non-destructive inspection device in claim 4, wherein the signal processing circuit including a display wherein the result of the first resulting signal and the second resulting signal is compensated by the compensator to produce the corrected resulting signals on the display.

10. The eddy current non-destructive inspection device in claim 4, wherein the first inspection frequency processing portion and the second inspection frequency processing portion each further comprising a corresponding low pass filter.

11. The eddy current non-destructive inspection device in claim 4, wherein the first inspection frequency processing portion and the second inspection frequency processing portion including a null circuit configured to enable a nulling process.

12. The eddy current non-destructive inspection device in claim 1 wherein the signal generating circuit including a low frequency signal generator generating a base low frequency signal.

13. The eddy current non-destructive inspection device in claim 12, wherein the low frequency processing portion further comprising a multiplier multiplying the signals received from the signal generating circuit and the base low frequency signal.

14. The eddy current non-destructive inspection device in claim 1, wherein the low frequency processing portion further comprising a low pass filter.

15. The eddy current non-destructive inspection device in claim 1, wherein the low frequency signal is a DC signal.

16. A method of configuring an eddy current non-destructive inspection device, wherein the inspection device including an eddy current probe having a probe circuit including coil components wherein the passage of a probe current through the probe circuit is effective to induce eddy currents in a test object when the probe and the test object are coupled, and the probe is effective to sense the eddy currents, wherein the probe circuit has a dynamically changing probe resistance,
   wherein the method comprising the steps of,
   generating an at least one inspection frequency signal and a low frequency AC signal, wherein the inspection frequency signal processes the sensed eddy currents to sensed signal, wherein the at least one inspection frequency signal affects the eddy currents and the sensed signal;
   receiving and processing the sensed signal and producing resulting signals by using a processing circuit, the resulting signal including a signal drift caused by change in coil conditions including temperature change, wherein the processing circuit further comprising at least one compensator,
   conducting coil monitoring by detecting the low frequency AC signal, applying a low pass filter and calculating a compensated value of the probe resistance with the signal drift annihilates and by which further deriving at least one compensation operation,
   correcting the resulting signals and producing corrected resulting signals based on at least one predetermined compensating operation that includes the compensated value of the dynamic probe resistance.

17. The method of configuring the eddy current non-destructive inspection device in claim 16 wherein the inspection signal and the low frequency signal and their corresponding resulting signals co-exist within at least a part of the signal generating circuit and the processing circuit.

18. The method of configuring the eddy current non-destructive inspection device in claim 16, wherein receiving and processing sensed signal and producing resulting signal including producing a first resulting signal and a second resulting signal.

19. The method of configuring the eddy current non-destructive inspection device in claim 18, wherein the at least one compensating operation is configured according to the compensated value of the probe resistance and is further attributed to at least one of the following:
   a) the first resulting signal;
   b) the second resulting signal;
   c) the inspection frequency.

20. The method of configuring the eddy current non-destructive inspection device in claim 16 further comprising configuring the at least one compensation operation from a chart or table exhibiting the effects of temperature changes on the probe circuit, wherein the chart or the table is derived from an electronic simulation or experiment on the probe circuit.

* * * * *